US011685852B2

(12) United States Patent
Patel et al.

(10) Patent No.: US 11,685,852 B2
(45) Date of Patent: Jun. 27, 2023

(54) RESERVOIR DRILLING FLUIDS CONSIST OF CATIONIC HETEROCYCLIC POLYMERS, SYNTHESIS, FORMULATION, AND APPLICATIONS

(71) Applicant: ARAMCO SERVICES COMPANY, Houston, TX (US)

(72) Inventors: Hasmukh A. Patel, Katy, TX (US); Carl Thaemlitz, Cypress, TX (US)

(73) Assignee: ARAMCO SERVICES COMPANY, Houston, TX (US)

( * ) Notice: Subject to any disclaimer, the term of this patent is extended or adjusted under 35 U.S.C. 154(b) by 113 days.

(21) Appl. No.: 17/011,285

(22) Filed: Sep. 3, 2020

(65) Prior Publication Data
US 2022/0064513 A1 Mar. 3, 2022

(51) Int. Cl.
*C09K 8/12* (2006.01)
*C07D 471/08* (2006.01)
*C07D 471/22* (2006.01)

(52) U.S. Cl.
CPC .............. *C09K 8/12* (2013.01); *C07D 471/08* (2013.01); *C07D 471/22* (2013.01)

(58) Field of Classification Search
CPC . C09K 8/12; C09K 8/035; C09K 8/24; C07D 471/08; C07D 471/22
See application file for complete search history.

(56) References Cited

U.S. PATENT DOCUMENTS

| | | | | |
|---|---|---|---|---|
| 3,760,819 A | * | 9/1973 | Vogt | A61K 8/4966 424/70.2 |
| 4,409,110 A | | 10/1983 | Borchardt et al. | |
| 4,652,384 A | | 3/1987 | Francis et al. | |
| 5,855,244 A | * | 1/1999 | Ahmed | C09K 8/24 166/295 |
| 2013/0000911 A1 | * | 1/2013 | Reddy | C09K 8/887 507/224 |
| 2015/0013984 A1 | | 1/2015 | Abivin et al. | |

FOREIGN PATENT DOCUMENTS

| | | | | | |
|---|---|---|---|---|---|
| CN | 106367043 A | * | 2/2017 | ............. | C09K 8/035 |
| CN | 106367043 A | | 2/2017 | | |
| CN | 106398662 A | * | 2/2017 | ............. | C09K 8/035 |
| CN | 106398662 A | | 2/2017 | | |
| CN | 104152123 B | | 3/2018 | | |
| CN | 109232781 A | | 1/2019 | | |
| EP | 0175412 B1 | | 8/1990 | | |
| KR | 20160097018 A | | 8/2016 | | |
| WO | 199722638 A1 | | 6/1997 | | |
| WO | WO 97/22638 | * | 6/1997 | | |

OTHER PUBLICATIONS

Liu, Ai-Wen and Hong-Biao Chen, "Synthesis and Characterization of 2,4,6-Tris(Methyl)-1,3,5-Benzenetricarboxal dyhyde", Chinese Journal of Sprectroscopy Laboratory, Issue 2, 2012, pp. 1062-1064 (7 pages).
Kolesinska, Beata et al., "Synthesis and cytotoxicity studies of bifunctional hybrids of nitrogen mustards with potential enzymes inhibitors based on melamine framework", Journal of Enzyme Inhibition and Medicinal Chemistry, Informa UK, Ltd., vol. 27, No. 5, 2012, pp. 619-627 (9 pages).
Catalano, Luca et al., "Dynamic Characterization of Crystalline Supramolecular Rotors Assembled through Halogen Bonding", Journal of the American Chemical Society, ACS Publications, American Chemical Society, vol. 137, Nov. 2015, pp. 15386-15389 (4 pages).
Walsh, Rosa Bailey et al., "Crystal Engineering through Halogen Bonding: Complexes of Nitrogen Heterocycles with Organic Iodides", Crystal Growth & Design, American Chemical Society, vol. 1, No. 2, Feb. 2001, pp. 165-175 (11 pages).
Yuan, Yuan et al., "Copolymers with both soft and rigid cationic rings as highly selective antimicrobials to combat antibiotic resistant microbes and biofilms", Journal of Materials Chemistry B, Sep. 2019, DOI: 10.1039/C9TB01264H (8 pages).
Boul, Peter J. et al., "High Performance Brine Viscosifiers for High Temperatures", SPE-183964-MS, Society of Petroleum Engineers, Mar. 2017 (21 pages).
Hamed, Samira Baba and Mansour Belhadri, "Rheological properties of biopolymers drilling fluids", Journal of Petroleum Science and Engineering, ScienceDirect, Elsevier B.V., vol. 67, 2009, pp. 84-90 (7 pages).
Luo, Zhihua et al., "Influence of an ionic liquid on rheological and filtration properties of water-based drilling fluids at high temperatures", Applied Clay Science, ScienceDirect, Elsevier B.V., vol. 136, 2017, Available online Nov. 2016, pp. 96-102 (7 pages).
Luo, Zhihua et al., "A novel star-shaped copolymer as a rheology modifier in water-based drilling fluids", Journal of Petroleum Science and Engineering, ScienceDirect, Elsevier B.V., vol. 168, May 2018, pp. 98-106 (9 pages).
Xie, Binqiang et al., "Rheological properties of bentonite-free water-based drilling fluids with novel polymer viscosifier", Journal of Petroleum Science and Engineering, Elsevier B.V., vol. 164, 2018, 302-310 (9 pages).

(Continued)

*Primary Examiner* — Kumar R Bhushan
(74) *Attorney, Agent, or Firm* — Osha Bergman Watanabe & Burton LLP

(57) ABSTRACT

A wellbore fluid may include a base fluid and at least one cationic heterocyclic polymer in an amount effective to increase a viscosity of the base fluid, the cationic heterocyclic polymer includes at least two distinct cyclic monomers, at least one of which has at least two heteroatoms in the cyclic structure. A method of drilling a wellbore may introduce such wellbore fluid into the wellbore. A method of producing a cationic heterocyclic polymer may include reacting, in a solvent selected from the group that includes tetrahydrofuran, dioxane, dichloromethane, alcoholic solvents, chlorinated solvents, aromatic hydrocarbon solvents, or mixture thereof, at least two distinct cyclic monomers, at least one of which has at least two heteroatoms in the cyclic structure.

12 Claims, 4 Drawing Sheets

(56) References Cited

OTHER PUBLICATIONS

Shigeno, Masanori et al., "Construction of Biaryl Scaffolds from Iodoarenes and C-H Heteroarenes Using an Amide Base Generated in situ from Aminosilane and Fluoride Anion", Asian Journal of Organic Chemistry, Asian Chemical Editorial Society, Wiley Online Library, Wiley-VCH Verlag GmbH & Co. KGaA, vol. 7, 2018, pp. 2082-2086 (5 pages).
International Search Report and Written Opinion issued in Application No. PCT/US2021/048825, dated Jan. 3, 2022 (14 pages).

* cited by examiner

RESERVOIR DRILLING FLUIDS CONSIST OF CATIONIC HETEROCYCLIC POLYMERS, SYNTHESIS, FORMULATION, AND APPLICATIONS

BACKGROUND

During drilling operations, a drilling fluid, which may also be referred to as drilling mud, is circulated through the wellbore to cool the drill bit, to convey rock cuttings to the surface, or to support the wellbore against collapse of the wellbore and against intrusion of fluids from the formation, among other purposes. Drilling fluids are formulated to have certain fluid characteristics, such as density and rheology, for example, that allow the drilling fluid to perform these functions. When circulation stops, the drill cuttings must remain suspended in the fluid. Under certain extreme downhole conditions, such as excessive temperature, for example, some of the properties of the drilling fluid may be altered.

Drilling fluids are typically classified according to their base fluid. In water-based muds (WBM), solid particles are suspended in water or brine. Oil can be emulsified in the water phase. Oil-based muds (OBM) are the opposite: solid particles are suspended in oil and water or brine is emulsified in the oil phase. OBM may contain diesel, mineral oil, esters, or alpha-olefins. Environmental concerns associated with the loss of the whole OBM in the formation, discharge of cuttings, and disposal of the OBM but also economic considerations have led to the increasing use of WBM in applications where OBM have previously been preferred. However, the exploration of deep oil and gas reservoirs requires the development of sophisticated drilling technologies to work at high temperatures and high pressures. OBM can be formulated to withstand high temperatures over long periods of time. However, WBM can break down and lead to loss of viscosity and fluid loss control at these high temperatures.

Generally, WBMs are composed of sodium bentonite, water and chemical additives, e.g. polymers, surfactants, fluid loss additives, etc. to modify the fluid's properties. In particular, the fluid's rheological property that reflects the flow and deformation of muds can be controlled to meet the demands of cuttings-transportation and hole-cleaning during drilling. Additional important functions of drilling fluids include wellbore stability maintenance and simultaneous control of the mud liquid-phase (filtration) penetration into a formation.

In general, for WBM systems, bentonite is suspended in water, which acts as the continuous phase. Various additives are introduced to obtain desired properties to meet the demands of the drilling. Water-soluble polymers are often used to adjust the rheological and filtration performances of the WBM. Biopolymers and certain synthetic polymers, such as starch, xanthan gum, carboxymethyl cellulose, and part-hydrolyzed polyacrylamide are widely used in drilling fluids. However, these polymers degrade rapidly at high temperatures, resulting in a poor performance. Synthetic polymers, e.g. acrylamide-based polymers, have also been employed as viscosifiers; however, these polymers tend to generate high viscosity upon mixing with an aqueous base fluid, which can delay drilling operations.

Thus, one of the vital components of the WBM is viscosifier or rheological modifier. While several natural and synthetic polymers have been employed for providing required drilling fluid properties, the traditional viscosifiers tend to lose their effectiveness at high temperature because of the thinning of the fluids.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a wellbore fluid that includes a base fluid and at least one cationic heterocyclic polymer in an amount effective to increase a viscosity of the base fluid, the cationic heterocyclic polymer includes at least two distinct cyclic monomers, at least one of which has at least two heteroatoms in the cyclic structure.

In another aspect, embodiments disclosed herein relate to a method of drilling a wellbore by introducing a wellbore fluid into the wellbore, wherein the wellbore fluid that includes a base fluid and at least one cationic heterocyclic polymer that includes at least two distinct cyclic monomers, at least one of which has at least two heteroatoms in the cyclic structure.

In another aspect, embodiments disclosed herein relate to a method of producing a cationic heterocyclic polymer that includes reacting, in a solvent selected from the group that includes tetrahydrofuran, dioxane, dichloromethane, alcoholic solvents, chlorinated solvents, aromatic hydrocarbon solvents, or mixture thereof, at least two distinct cyclic monomers, at least one of which has at least two heteroatoms in the cyclic structure.

Other aspects and advantages of this disclosure will be apparent from the following description made with reference to the accompanying drawings and the appended claims.

DETAILED DESCRIPTION

Figure 1:
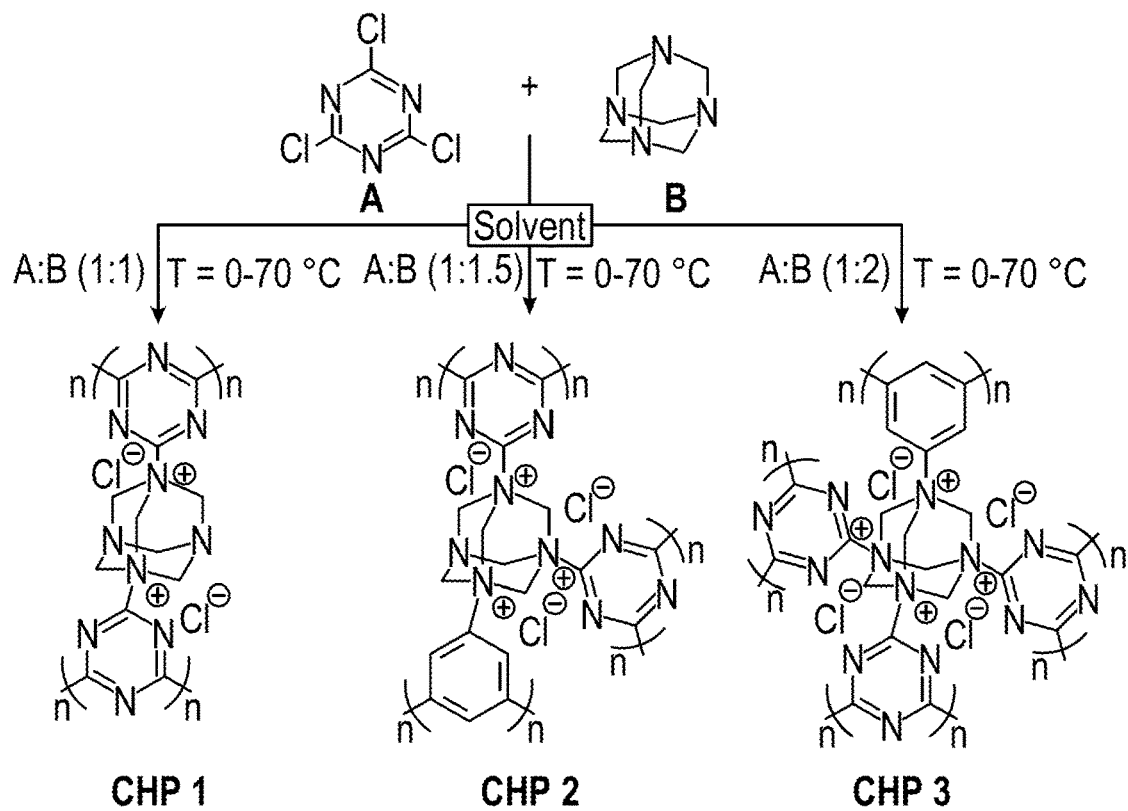
FIG. 1 depicts a schematic illustration of synthetic pathways for cationic heterocyclic polymers according to one or more embodiments.

Embodiments disclosed herein generally relate to water-based wellbore fluids that include a cationic heterocyclic polymer, as well as methods of making such cationic heterocyclic polymers, and methods of using such fluids. In particular, such fluids may have particular suitability for use in reservoir drilling fluid (RDF) applications.

Reservoir drilling fluids are specially designed to drill the reservoir zone successfully, minimize damage to the formation and maximize reservoir production. Reservoir drilling fluids must also protect the formation from damage and the negative impact on reservoir production that results therefrom.

As mentioned, wellbore fluids generally contain at least one polymer (including natural and synthetic polymers) used to adjust the rheological and filtration performances of a WBM. However, conventional viscosifiers tend to lose their effectiveness at high temperature because of the thinning of the fluids. For instance, while biopolymers and certain synthetic polymers, such as starch, xanthan gum, carboxymethyl cellulose, and part-hydrolyzed polyacrylamide are widely used in drilling fluids, these polymers degrade rapidly at high temperatures, resulting in a poor rheological performance. Another disadvantage associated with conventional synthetic polymer-based viscosifiers is high viscosity generation upon mixing with base fluids, i.e. water or brine. A very high viscosity or plastic viscosity may have serious consequences when pumping reservoir drilling fluids, causing unintentional damage to the reservoir zone.

Advantageously, the cationic heterocyclic polymers of the present disclosure may provide greater thermal stability than conventional viscosifiers, thereby allowing the polymeric viscosifiers to be used in higher temperature wells, and may have particular suitability for use in reservoir drilling fluids.

While the scope of the composition and method will be described with several embodiments, it is understood that one of ordinary skill in the relevant art will appreciate that many examples, variations and alterations to the composition and methods described here are within the scope and spirit of the disclosure. Accordingly, the embodiments described are set forth without any loss of generality, and without imposing limitations, on the disclosure. Those of skill in the art understand that the scope includes all possible combinations and uses of particular features described in the specifications.

One or more embodiments of the present disclosure relate to a wellbore fluid that includes a base fluid and at least one cationic heterocyclic polymer (CHP) in an amount effective to increase viscosity of the base fluid. The CHP has recurring units derived from at least two distinct cyclic monomers, at least one of which has at least two heteroatoms in the cyclic structure.

Cyclic Monomers

The heterocyclic polymers of the present disclosure may be formed from at least two distinct monomers, both of which are cyclic monomers. In one or more embodiments, one of the at least two cyclic monomers has at least two heteroatoms in the cyclic structure.

One of the at least two distinct cyclic monomers is a halogenated monomer selected from cyanuric chloride or halogenated compounds having a benzene-ring containing halogenation in 1,3,5 positions or 1,4 positions. For example, the halogenated monomer may be selected from the group consisting of:

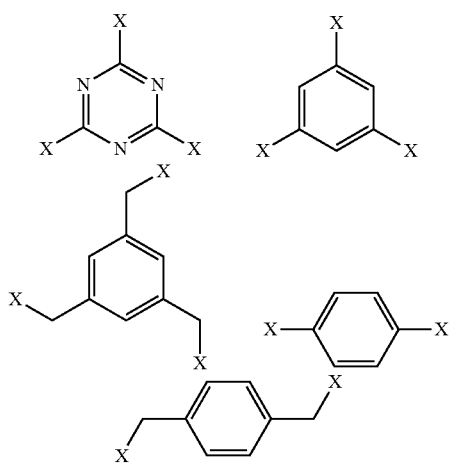

wherein each X is selected from Cl, Br, or I.

In one or more embodiments, another of the at least two distinct cyclic monomers is a non-halogenated nitrogen-rich heterocycle. In one or more embodiments, the non-halogenated nitrogen-rich heterocycle may include at least two nitrogens in the cyclic structure. For example, the non-halogenated nitrogen-rich heterocycle may be selected from the group consisting of 1,4-diazabicyclo[2.2.2]octane, hexamethylenetetramine, pyrazine and bipyridine, wherein a pyrazine or bipyridine is optionally substituted by hydroxyl or alkyl groups, or combinations thereof. In one or more embodiments, the non-halogenated monomer may be selected from:

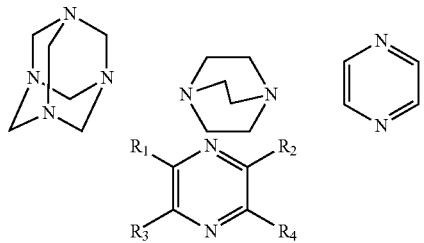

where each of $R_1$, $R_2$, $R_3$, and $R_4$ may individually be selected from hydrogen, hydroxyl, thiol, nitrile, azide, alkyl functionalities, or combinations thereof. Exemplary alkyl functionalities may include $C_1$-$C_3$ alkyl groups. Thus, in one or more embodiments, the non-halogenated nitrogen-rich monomer may be at least bicyclic. In one or more other embodiments, the non-halogenated monomer may be a heterocyclic aromatic monomer.

Upon polymerizing the two distinct monomers, the nitrogen-rich heterocyclic monomer reacts, at the nitrogen(s), with the halogenated monomer, thereby resulting in a cationic polymer counterbalanced by counter anions selected from chloride, bromide, iodide, hydroxide anions, or mixture thereof.

Polymer

Polymers formed by the aforementioned monomers may result in a cationic heterocyclic polymer. Thus, the cyclic monomers maintain their cyclic structure in the resulting polymer, and the presence of at least one heterocyclic monomer results in the polymer containing recurring heterocyclic units as well. With one of the two (at least) monomers having two heteroatoms in the cyclic structure, the reaction between the two, by nucleophilic aromatic substitution, results in the polymer having an aromatic heterochain backbone, and with cationic sites on the backbone. Further, based on the number of reaction sites between the two monomer species, the respective monomers react to form two dimensional sheet type of polymer architectures (for the backbone), in one or more embodiments, and three dimensional network polymers because of reactions between trifunctional and difunctional monomers. Thus, in one or more embodiments, the backbone of the CHP extends in at least two dimensions.

Figure 2:
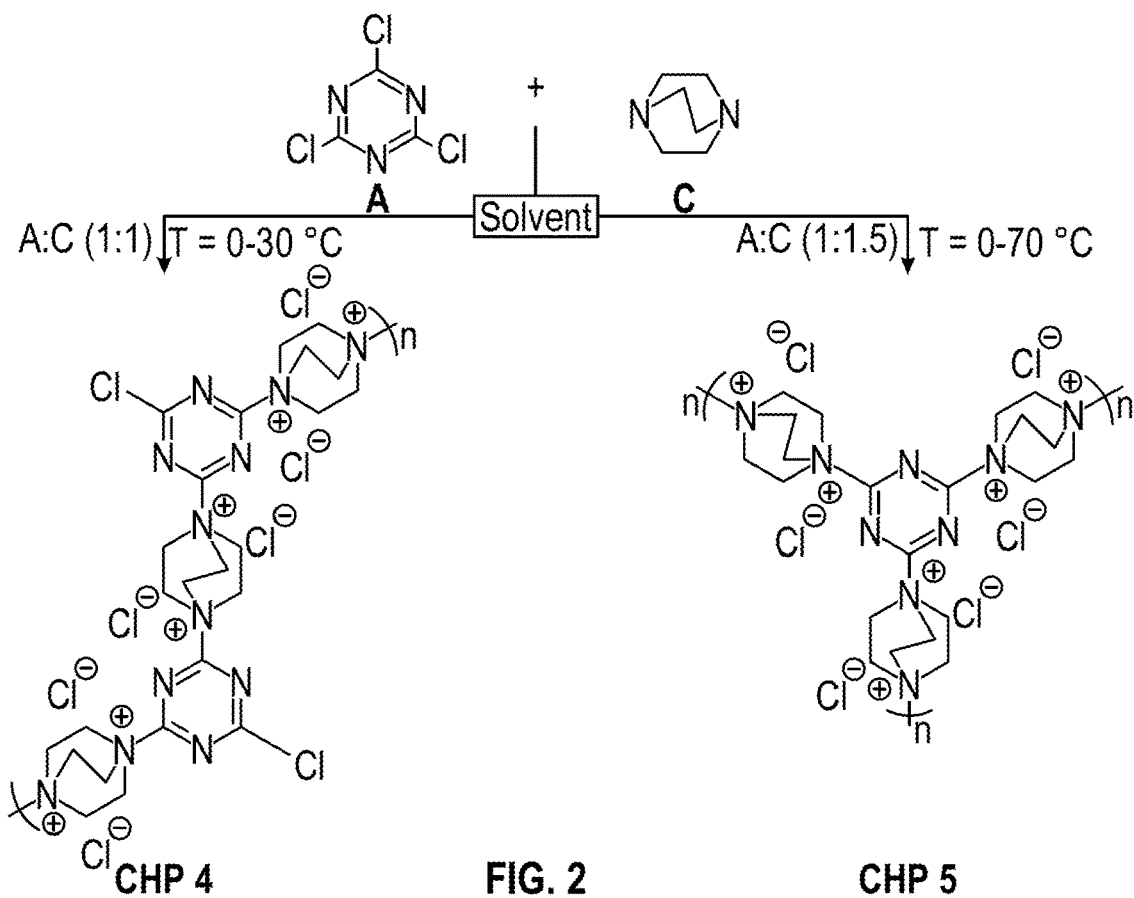
FIG. 2 shows a schematic representation depicting synthetic pathways for cationic heterocyclic polymers according to one or more embodiments.

The multi-dimensional nature of the CHPs of the present disclosure may be observed in FIG. 1 and FIG. 2, which shows example reaction pathways to obtain various CHPs. In particular, FIG. 1 depicts a schematic representation of the synthetic pathways for cationic heterocyclic polymers (CHP-1, CHP-2 and CHP-3) generated from different molar ratios of a halogenated aromatic compound, specifically cyanuric chloride (monomer A) as shown, and a nitrogen-rich heterocycle, specifically hexamethylenetetramine (monomer B) shown. As shown, in FIG. 1, by varying the molar ratio of the halogenated aromatic compound and the nitrogen-rich heterocycle, for example from 1:1, 1:1.5, and 1:2, different polymer structures may be formed. Similarly, FIG. 2 shows a schematic representation depicting the synthetic pathways for cationic heterocyclic polymers (CHP-4 and CHP-5) generated from different molar ratios of a halogenated aromatic compound, specifically cyanuric chloride (monomer A) as shown, and a nitrogen-rich heterocycle, specifically 1,4-Diazabicyclo[2.2.2]octane (DABCO) (monomer C). As shown in FIG. 2, by varying the molar ratio of the halogenated aromatic compound and the nitrogen-rich heterocycle, for example from 1:1 and 1:1.5, different polymer structures may be formed. FIGS. 1 and 2 also both illustrate that the CHPs of the present disclosure are synthesized through atom efficient routes, meaning the mixing of two monomers will result in the product without any byproducts.

Depending on the polymeric structure desired, the molar ratio between the halogenated aromatic monomer and the non-halogenated heterocycle may vary from 1:2 to 1:0.2. For example, it may have a lower limit of any of 1:2, 1:1.75, 1:5, 1:1.2, or 1:1, and an upper limit of any of 1:1, 1:0.75, 1:0.5, 1:0.25, or 1:0.2, wherein any lower limit can be used in combination with any upper limit.

In one or more embodiments, the CHPs may have an weight average molecular weight (Mw) ranging from a lower limit of any of 10, 50, or 75 kDa, and an upper limit of any of 100, 500, or 1000 kDa, where any lower limit may be used in combination with any upper limit.

In one or more embodiments, the counter anions in the CHPs may be chloride, bromide, iodide, hydroxide, or mixture thereof.

In one or more embodiments, the CHPs may have a thermal stability, measured by thermogravimetric analyses, in both inert and oxidative atmospheres ranging from a lower limit of any of 150, 175, or 200° C., to an upper limit of any of 200, 225, and 250° C., where any lower limit can be used in combination with any upper limit. See FIG. 6.

Synthesis

In another aspect, embodiments disclosed herein also relate to a method of producing a cationic heterocyclic polymer (CHP) such as those described above. As mentioned, the polymer synthesis may be atom efficient, meaning the mixing of two monomers will result in the product without any byproducts.

The synthesis may occur by reacting the at least two cyclic monomers in a solvent at a reaction temperature.

In one or more embodiments, the solvent may be selected from the group consisting of tetrahydrofuran, dioxane, dichloromethane, alcoholic solvents, chlorinated solvents, aromatic hydrocarbon solvents, or mixtures thereof. For example, in one or more embodiments, each monomer may be added independently to a volume of solvent and mixed therein before the two monomers (in solvent) are added together for reaction.

In one or more embodiments, the monomer to solvent ratio (weight/volume) may range from a lower limit of any of 2, 5, or 10 g/mL to an upper limit of any of 15, 25, or 50 g/100 mL, where any lower limit is used in combination with any upper limit.

In one or more embodiments, the reaction temperature may range from 0° C. to 70° C. For example, the reaction temperature may have a lower limit of any of 0, 2, 10, or 20° C., and an upper limit of any of 40, 50, 60, or 70° C., where any lower limit can be used in combination with any upper limit. In one or more embodiments, the monomer may be initially reacted at a first temperature for a period of time, and then the reaction temperature may be raised to at least a second, more elevated temperature. The total reaction time may vary, for example, from 2 to 24 hours, such as from a lower limit of any of 2, 4, or 6 hours, and an upper limit of any of 6, 10, 18, or 24 hours, where any lower limit can be used in combination with any upper limit. It is envisioned that the reaction may proceed at the first, lower temperature for up to 2 hours, for example, prior to the temperature being raised to the second, higher reaction temperature. Such first, lower temperature may be in a range, for example, of 10 to 15° C. Following the end of the reaction time, the precipitates formed may be filtered and dried.

Wellbore Fluids and Uses Thereof

Embodiments disclosed herein are directed to a wellbore fluid that includes a base fluid and at least one CHP, such as those described above, in an amount effective to increase the viscosity of the base fluid.

In one or more embodiments, the amount of CHP present in the wellbore fluid may range from a lower limit of any of 0.2, 0.5, or 1.0 g/100 mL of base fluid, to an upper limit of any of 1.25, 2, or 3 g/100 mL of base fluid, where any lower limit can be used in combination with any upper limit.

In one or more embodiments, the base fluid may be an aqueous base fluid. An aqueous base fluid may be any suitable fluid such as water or a solution containing both water and one or more organic or inorganic compounds dissolved in the water or otherwise completely miscible with the water. For example, in some embodiments, the aqueous base fluid may include at least 50 wt. % water. The aqueous base fluid may include one or more of fresh water, well water, filtered water, distilled water, sea water, salt water, produced water, formation brine, other type of water, or combinations of waters. Salts that may be present include but are not limited to alkali metal chlorides, hydroxides, or carboxylates. In some embodiments, suitable salts may include sodium, calcium, cesium, zinc, aluminum, magnesium, potassium, strontium, silicon, lithium, chlorides, bromides, carbonates, iodides, chlorates, bromates, formates, nitrates, sulfates, phosphates, oxides, fluorides and combinations of these. In one or more embodiments, the base fluids may be a brine that includes at least one salt selected from sodium bromide (NaBr), sodium chloride (NaCl), calcium chloride ($CaCl_2$), potassium chloride (KCl), zinc chloride ($ZnCl_2$), cesium formate (HCOOCs), potassium formate (HCOOK), sodium formate (HCOONa) and potassium iodide (KI). Brines can be tailored to particular well conditions with a broad range of salts. Typical brines can have densities between about 1 gram per cubic centimeter ($g/cm^3$) and about 2.4 $g/cm^3$ at standard temperature and pressure.

In one or more embodiments, in addition to the CHP and base fluid, the wellbore fluid may also include at least one surfactant, which may be an anionic surfactant. Examples of anionic surfactants include alkylbenzene sulfonates (such as dodecylbenzene sulfonates, sodium dodecyl sulfate, sodium salt of fatty acids), alkyl sulfonates, alkyl sulfates (such as sodium dodecyl sulfate), alkyl ether sulfates, salts of fatty acids (such as sodium salts of fatty acids), and combinations of the same. In one or more embodiments, the anionic surfactant may be present at a weight ratio, relative to the CHP, ranging from 0.2:1 to 1:1.

The density of the fluids may be tailored through the brine selected, or may optionally include at least one solid weighting agent therein. A weighting agent refers to finely divided solid material that is used to increase the density of a wellbore fluid. Non-limiting examples of weighting agents include barite, hematite, calcium carbonate, siderite, and ilmenite, manganese oxide, iron oxides and their various minerals, barium sulfate, barium oxide, barium hydroxide, barium chloride.

The wellbore fluid can also include a viscosifying polymer, including biopolymers and modified biopolymers and synthetic polymers. Nonlimiting examples of viscosifying biopolymers include carboxymethyl cellulose, lignosulfonate, hydroxyethyl cellulose, guar gum, xanthan gum, and hydroxypropyl guar. Nonlimiting examples of viscosifying synthetic polymers include amine/amide fatty acid copolymers, acrylates and acrylate copolymers, hydrolyzed polyacrylamide and their ionic salts, maleic anhydride and styrene copolymers based polymers. Generally, the viscosifying effect of a biopolymer is degraded as temperature increases. However, the CHPs of the present disclosure may improve and maintain the viscosifying effect of the biopolymer at temperatures which otherwise would result in the complete loss of the viscosifying effect of the biopolymer alone.

The wellbore fluids of the present disclosure may also include additional components such as fluid loss additives, shale inhibitors, alkalinity control agents, bridging agents, pH buffers, known to one of ordinary skill in the relevant art.

The wellbore fluids of the present disclosure may be prepared by combining the CHPs disclosed herein with an intermediate wellbore fluid composition. As used here, the term "intermediate wellbore fluid composition" refers to a composition made in the process of preparing a wellbore fluid before the CHP is added, the composition having at least one wellbore fluid component (such as brine, biopolymer, surfactant, shale inhibitor, fluid loss additive, weighting agent, etc.) without the CHP. In some embodiments the present fluids may be prepared by mixing the CHP with the intermediate wellbore fluid composition for a period of time, and then adding and mixing one or more additional wellbore fluid components at spaced intervals. By way of example and not limitation, the wellbore fluid can be prepared by first mixing the water-based fluid with the biopolymer for a period of time (for example, five minutes. Then, following mixing the water-based continuous phase with the biopolymer, adding and mixing the CHP for a period of time (for example, five minutes), then adding and mixing the anionic surfactant for a period of time (for example, five minutes), and so forth; continuing in this manner with each additional desired wellbore fluid component. The mixing may be carried out such that shear forces are applied to the CHP and intermediate well fluid composition, such as by using a high-shear mixer.

In one or more embodiments, the wellbore fluid may be further prepared by aging the wellbore fluid mixture having the CHP therein. The aging process can be carried out by subjecting the fluid to and maintaining a pressure greater than atmospheric pressure and a temperature greater than ambient temperature for a period of time, such as in a hot rolling oven.

In one or more embodiments, the wellbore fluid may have a plastic viscosity (PV) within a range from 10 to 120 cP at a temperature ranging from 72 F to 450 F, and a pressure ranging from 15 psi to 35000 psi.

In one or more embodiments, the wellbore fluid may have a yield point (YP) that is within a range from 2 to 50 lb/100 ft$^2$ at a temperature ranging from 72 F to 450 F, and under a pressure ranging from 15 psi to 35000 psi.

One or more embodiments disclosed herein relate to a method of drilling a wellbore, comprising introducing the presently described wellbore fluids into the wellbore. In particular, the fluids being introduced into the wellbore may include a variety of wellbore fluids, such as drilling fluids, completion fluids, workover fluids, matrix stimulation and fracturing fluids, thickeners, diversion fluids, and many other applications where thickened or gelled aqueous compositions are desired. For example, in at least one embodiment, the present technology provides cationic heterocyclic polymers to improve the rheological properties of reservoir drilling fluids.

While the CHPs of the present disclosure may be used in any type of drilling fluid, i.e., any fluid used to aid the drilling of boreholes into subterranean formations, they may have particular applicability when used to drill the reservoir section of the well. Reservoir drilling fluids (also referred to as reservoir drill-in fluids or RDFs) may be formulated to be substantially free of solids, as there can be a concern that solids could plug pores in the formation and reduce hydrocarbon flow rates.

Completion fluids are also commonly solids-free fluids used to "complete" an oil or gas well, and are a type of fluid that the present disclosed CHPs may have particular utility. Specifically, this fluid is placed in the well to facilitate final operations prior to initiation of production, such as setting screens production liners, downhole valves or shooting perforations into the producing zone. The fluid is meant to control a well should downhole hardware fail, without damaging the producing formation or completion components.

Completion, workover, and kill pill fluids are designed to prevent fluid from the formation intruding into the wellbore while preventing wellbore fluid leakoff. Leakoff is the loss of fluid from the wellbore into the formation. Fluid leakoff is known to cause formation damage, potentially reducing hydrocarbon recovery. As used in this disclosure, "workover fluids" are fluids used during workover operations of a wellbore such as during repair or stimulation of an existing production well for the purpose of restoring, prolonging or enhancing the production of hydrocarbons from the production well. In one or more embodiments, the presently described CHPs may be incorporated into a workover fluid.

EXAMPLES

Example 1

CHP-1 is formed by mixing cyanuric chloride and hexamethylenetetramine at a molar ratio of 1:1. In a reaction vessel, 14 g (0.1 mol) of hexamethylenetetramine was mixed with 300 mL tetrahydrofuran at room temperature, and the reaction mixture was cooled to 0° C. The cyanuric chloride (18.4 g, 0.1 mol) is dissolved in 100 mL of tetrahydrofuran in a separate vessel. The cyanuric chloride solution was added to hexamethylenetetramine solution with stirring for over 30 min. The reaction temperature was maintained at 0-5° C. for one hour. Subsequently, the reaction mixture was heated to room temperature (25-30° C.) and stirred at this temperature for 5 to 6 hours. The temperature of the reaction mixture was increased to 70° C. and stirred at this temperature for 18 hours. The precipitates formed were filtered and dried at 80-100° C. for 5 hours in vacuum oven.

Example 2

CHP-2 is formed by mixing cyanuric chloride and hexamethylenetetramine at a molar ratio of 1:1.5. In a reaction vessel, 21 g (0.15 mol) of hexamethylenetetramine was mixed with 300 mL tetrahydrofuran at room temperature and the reaction mixture was cooled to 0° C. Cyanuric chloride (18.4 g, 0.1 mol) was dissolved in 125 mL tetrahydrofuran in a separate vessel. The rest of the process is similar to Example 1.

Example 3

CHP-3 is formed by mixing cyanuric chloride and hexamethylenetetramine at a molar ratio of 1:2. In a reaction vessel, 28 g (0.2 mol) of hexamethylenetetramine was mixed with 300 mL tetrahydrofuran at room temperature and the reaction mixture was cooled to 0° C. Cyanuric chloride (18.4 g, 0.1 mol) was dissolved in 125 mL tetrahydrofuran in a separate vessel. The rest of the process is similar to Example 2.

Example 4

CHP-4 is formed by mixing cyanuric chloride and 1,4-Diazabicyclo[2.2.2]octane (DABCO) at a molar ratio of 1:1. In a reaction vessel, 11.2 g of DABCO (0.1 mol) was mixed with 200 mL tetrahydrofuran at room temperature and the reaction mixture was cooled to 0° C. Cyanuric chloride (18.4 g, 0.1 mol) was dissolved in 50 mL of tetrahydrofuran in a separate vessel. The cyanuric chloride solution was added to the DABCO solution with stirring for over 30 min. The reaction temperature was maintained at 0-5° C. for one hour. Subsequently, the reaction mixture is heated to room temperature (25-30° C.) and stirred at this temperature for 5 to 6 hours. The precipitates formed were filtered and dried at 80-100° C. for 5 hours in a vacuum oven.

Example 5

CHP-5 is formed by cyanuric chloride and DABCO at a molar ratio of 1:1.5. In a reaction vessel, 16.8 g of DABCO (0.15 mol) were mixed with 200 mL of tetrahydrofuran at room temperature and the reaction mixture was cooled to 0° C. The rest of the process is similar to Example 4.

Figure 3:
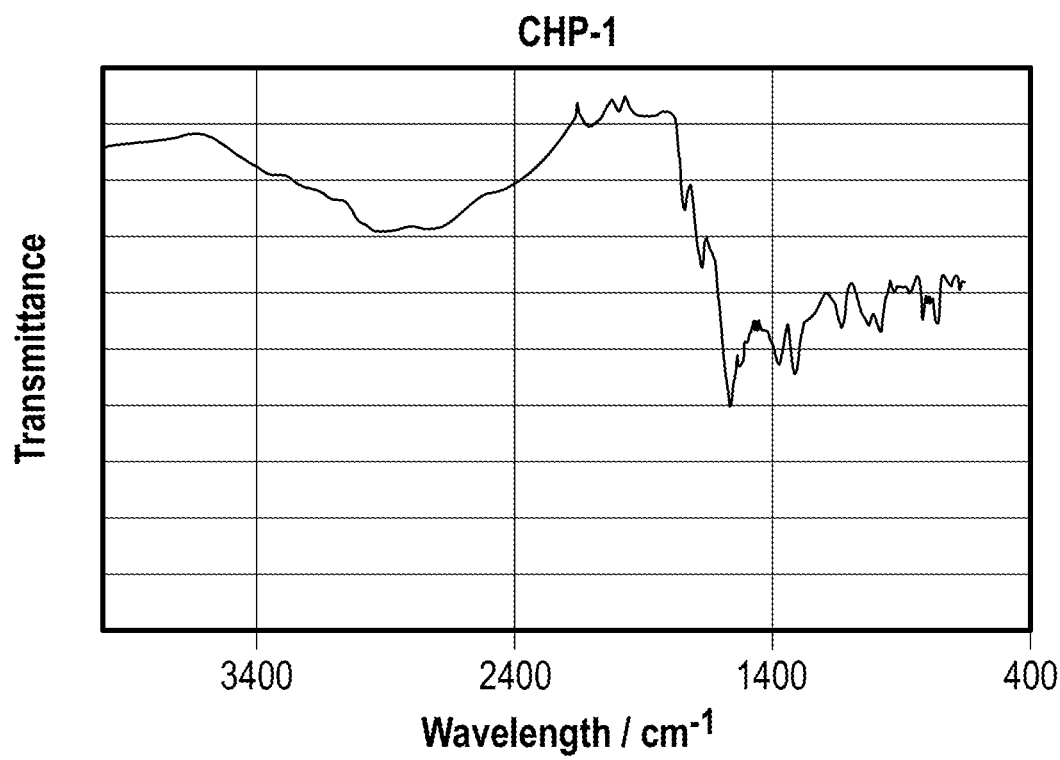
FIGS. 3-4 show FTIR spectra of cationic heterocyclic polymers indicating the formation of the desired products.
Figure 4:
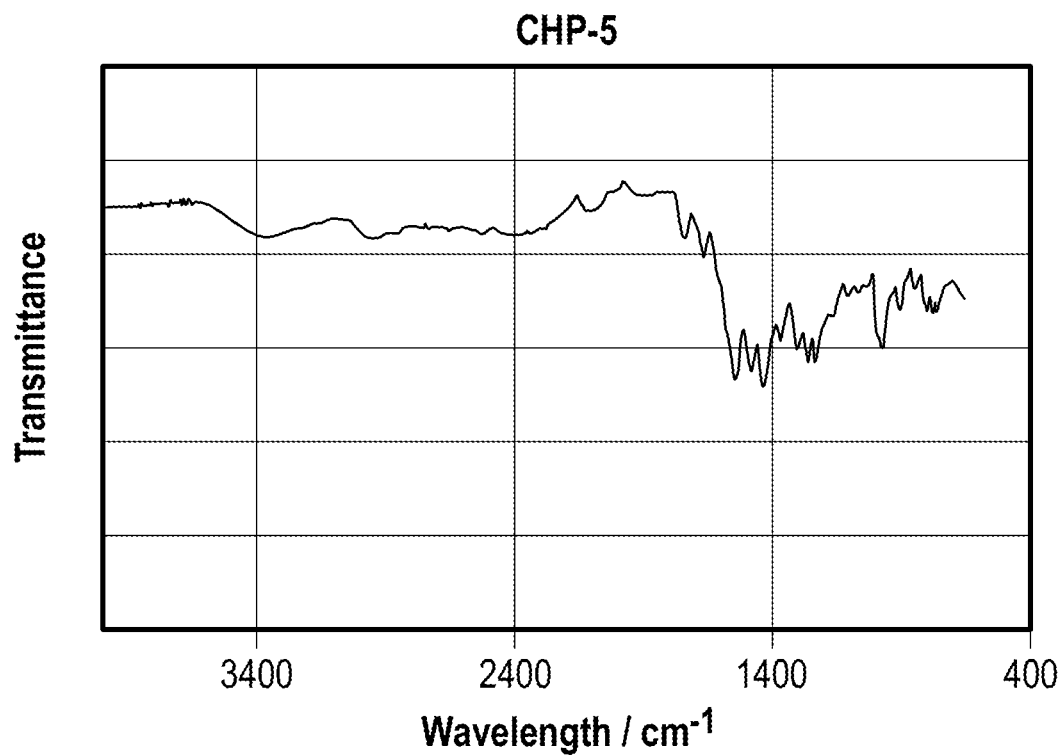

A spectroscopic analysis using a Fourier Transformed Infrared Spectrometer (Cary 630 FTIR Spectrometer, Agilent) of CHP-1 and CHP-5 was conducted to study the CHPs' structural information, as shown in FIGS. 3 and 4. The tertiary amine C-N stretching vibration from DABCO and hexamethylenetetraamine at 1052 cm$^{-1}$ disappears after the CHPs formation, indicating the successful quaternization of the core triazines. Since the resulting CHPs are highly charged, it attracts atmospheric water. Therefore, —OH vibrations are expected due to the adsorption of moisture during the analysis. In fact, CHPs show several bands around 1500 cm$^{-1}$ region, which corresponds to the typical stretching modes of C-N heterocycles. The band at 800 cm$^{-1}$ is from triazine moiety and the broad band at 3500 cm$^{-1}$ is coming from —OH vibration from water.

Figure 5:
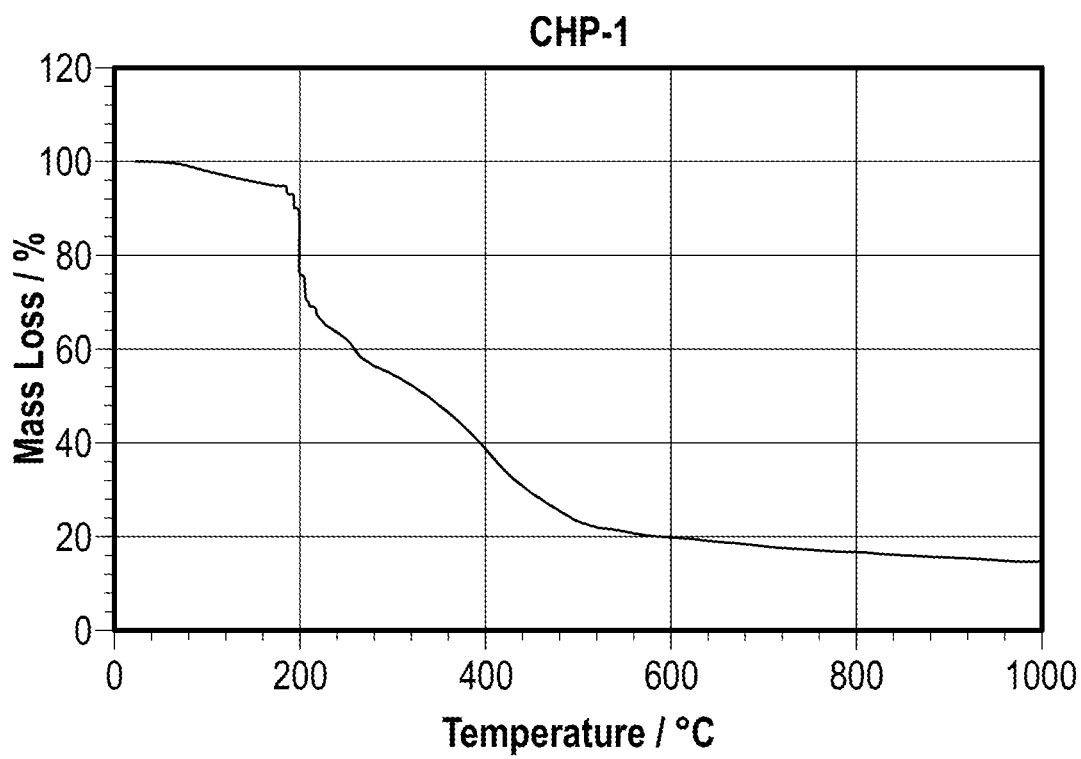
FIGS. 5-6 show thermogravimetric analysis of cationic heterocyclic polymers.
Figure 6:
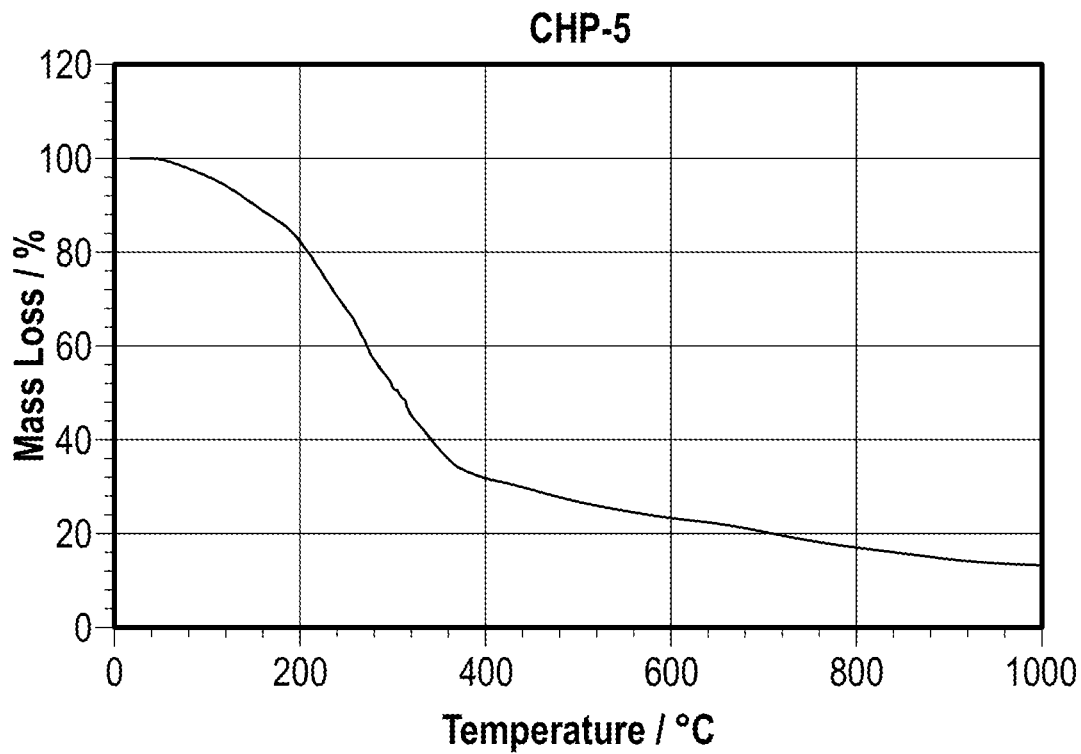

An evaluation of the thermal stability of CHP-1 and CHP-5 was performed by thermogravimetric analyses (SDT Q600, TA Instruments) up to 1000° C., shown in FIGS. 5 and 6. As shown, CHP-1 is stable up to 200° C. while CHP-5 is stable up to 150° C. The initial weight loss (<150° C.) in CHP-5 is associated with adsorbed water in the network of CHP-5. Therefore, the thermal stability of these polymer networks suggest that it may not degrade significantly below 200° C.

Example 6

In this example, three formulations of drilling fluids were prepared through high shear mixing of the components and the drilling fluid additives shown in Table 1 below. The three formulations show a comparison with and without CHPs. Specifically, fluids incorporating CHP-1 and CHP-5 from Examples 1 and 5 were used. RevDust (Ca-montmorillonite) was added in the drilling fluids to replicate the contamination in drilling fluids during drilling operations. Other additives, e.g. fluid loss additives, acid scavenger and pH control additive, were also incorporated to obtain stable drilling fluids. An anionic surfactant employed with CHPs in this example is sodium dodecyl benzenesulfonate.

TABLE 1

| Components | Drilling Fluid Formulations | | |
|---|---|---|---|
| | RDF-Ref. | RDF-CHP-1 | RDF-CHF-5 |
| NaBr Brine (12.5 ppg) | 408 gm | 408 gm | 408 gm |
| Xantham Gum | 0.5 gm | 0.5 gm | 0.5 gm |
| CHP-1 | — | 3.0 gm | — |
| CHP-5 | — | — | 3.0 gm |
| Sodium dodecylbenzene sulfonate | 3.0 gm | 3.0 gm | 3.0 gm |
| Fluid loss additive | 3.0 gm | 3.0 gm | 3.0 gm |
| MgO | 2.0 gm | 2.0 gm | 2.0 gm |
| Iron gluconate | 1.0 gm | 1.0 gm | 1.0 gm |
| Barite | 257.6 gm | 257.6 gm | 257.6 gm |
| RevDust | 40.0 gm | 40.0 gm | 40.0 gm |

The drilling fluids are prepared through high shear mixing of the components mentioned in Table 1 above. The order of mixing and time of shearing after adding each component are as follow for the three reservoir drilling fluids.

The base fluid for the Reference Reservoir Drilling Fluids (RDF-Ref.) is a sodium bromide (NaBr) fluid. Xanthan gum is added and mixed for 5 minutes. Then, sodium dodecylbenzene sulfonate is added and mixed for 5 minutes; then the fluid loss additive is mixed for 5 minutes; magnesium oxide (MgO) is mixed for 5 minutes and iron gluconate for 5 minutes as well. After that, barite is added and mixed for 10 minutes and RevDust mixed for an additional 10 minutes.

For the Reservoir Drilling Fluids with CHP-1 (RDF-CHP-1), CHP-1 is added to the NaBr base fluid after the addition of Xanthum gum and is mixed for 5 minutes. The solution is mixed for 5 minutes and then the same procedure as RDF-Ref. described above is reproduced.

For the Reservoir Drilling Fluids with CHP-5 (RDF-CHP-5), the same procedure as RDF-CHP-1 is reproduced but replacing CHP-1 with CHP-5.

The drilling fluids are poured into pressure vessels for aging. These vessels are pressurized to 500 psi with nitrogen gas. The drilling fluids are aged by hot-rolling at 300° F. for 16 hours. Then, the drilling fluids are cooled to room temperature where the rheological properties are measured. The ambient rheological properties were measured by the Rheometer (Fann 35, Fann Instruments).

TABLE 2

| | RDF-Ref. | | RDF-CHP-1 | | RDF-CHF-5 | |
|---|---|---|---|---|---|---|
| rpm | Before aging | After aging | Before aging | After aging | Before aging | After aging |
| 600 | 198 | 220 | 185 | 202 | 170 | 205 |
| 300 | 101 | 115 | 109 | 115 | 94 | 121 |
| 200 | 71 | 85 | 81 | 90 | 81 | 101 |
| 100 | 45 | 46 | 51 | 68 | 52 | 64 |
| 6 | 9 | 7 | 15 | 17 | 13 | 14 |
| 3 | 7 | 4 | 9 | 10 | 9 | 10 |

TABLE 2-continued

| rpm | RDF-Ref. | | RDF-CHP-1 | | RDF-CHF-5 | |
| --- | --- | --- | --- | --- | --- | --- |
| | Before aging | After aging | Before aging | After aging | Before aging | After aging |
| 10 sec (3 rpm) | 7 | 5 | 10 | 11 | 10 | 10 |
| 10 min (3 rpm) | 7 | 6 | 10 | 12 | 11 | 11 |
| Plastic viscosity, cP | 97 | 105 | 76 | 87 | 76 | 84 |
| Yield point | 4 | 10 | 33 | 28 | 18 | 37 |

The following rheological parameters were calculated from the data obtained from the rheometers:

Plastic Viscosity (PV)=600 rpm−300 rpm
Yield Point (YP)=300 rpm−PV
Apparent Viscosity=600 rpm/2
Low Shear Yield Point (LSYP)=2*3 rpm−6 rpm
10 s Gel—measured as 3 rpm maximum reading to break gel after 10 sec. rest
10 m Gel—measured at 3 rpm maximum reading to break gel after 10 min. rest.

As mentioned above, the rheological properties of drilling fluids are critical to the success of drilling operations. The development of oil and gas reservoirs at increasing depths require reservoir drilling fluids capable of maintaining their rheological properties at high temperatures and high pressures. Unexpected variation in rheological properties at high temperatures and pressures can result in poor hole cleaning, barite sagging, and lost circulation due to formation of cuttings bed and barite plug. Therefore, the rheological properties of the three drilling fluids were also studied at high pressure (10,000 psi) and high temperatures (150-400° F.) (HTHP) as well.

Figure 7:
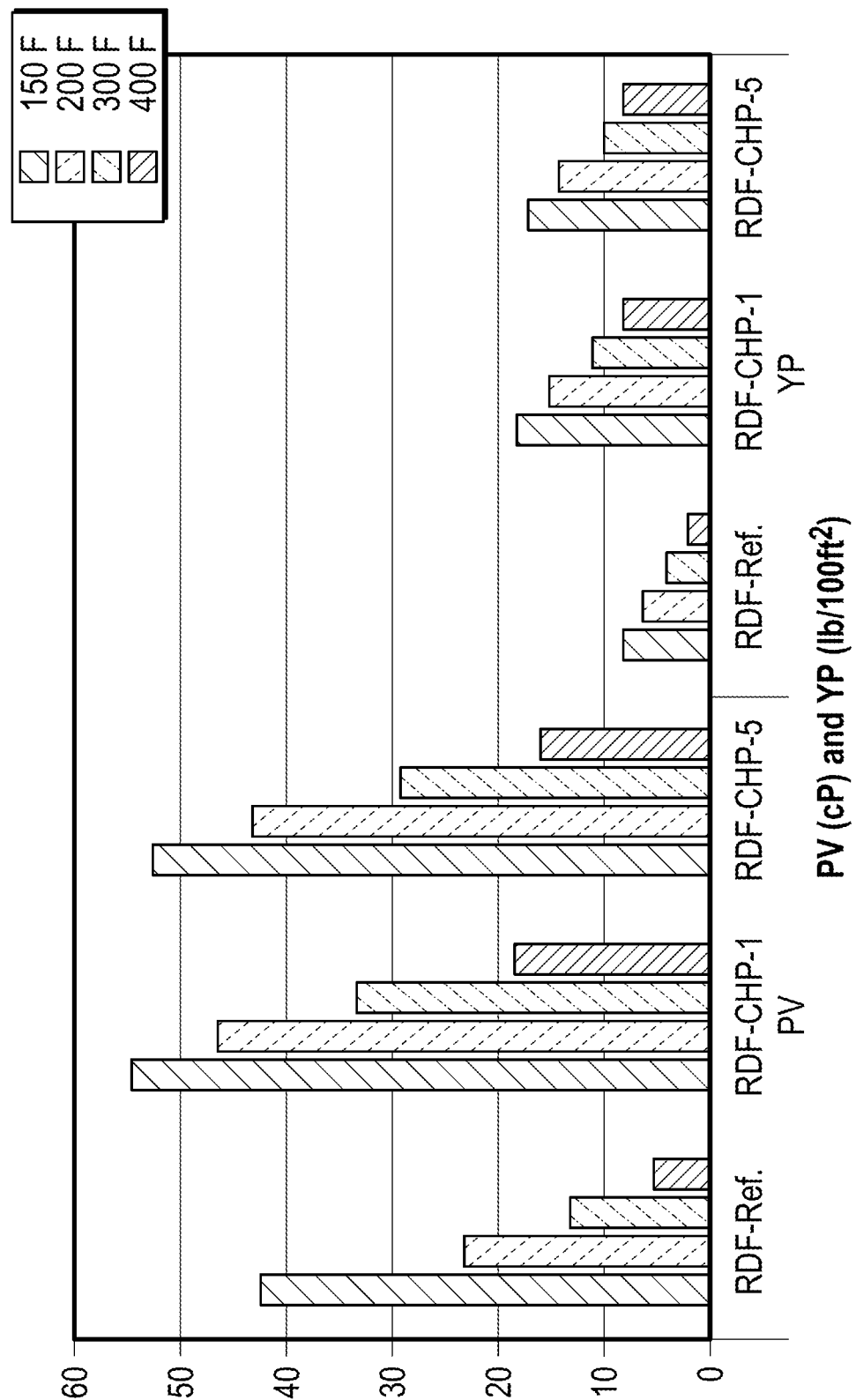
FIG. 7 shows the rheological properties of wellbore fluid formulations at high temperatures and a pressure of 10,000 psi.

The properties, e.g., PV and YP, were calculated from the data obtained from the HPHT Rheometer, the results of which are shown in FIG. 7. As shown, the Reservoir Drilling Fluid of Reference (RDF-Ref.) experiences a sharp drop of viscosity from 42 cP to 4 cP as the temperature increases from 150 F to 400 F. However, the viscosity of RDF-CHP-1 is better maintained going from 54 cP to 18 cP in the same temperature interval. RDF-CHP-5 goes from 52 cP to 16 cP from 150 F to 400 F. The yield point results are similar in that RDF-CHP-1 and RDF-CHP-5 better maintain their yield points as the temperature increases from 150 F to 400 F.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A wellbore fluid, comprising:
   a base fluid;
   an anionic surfactant; and
   at least one cationic heterocyclic polymer (CHP) in an amount effective to increase a viscosity of the base fluid, the CHP comprising at least two distinct cyclic monomers, at least one of which has at least two heteroatoms in the cyclic structure, wherein the CHP comprises a counter anion selected from the group consisting of a chloride anion, bromide anion, iodide anion, hydroxide anion, and mixtures thereof.

2. The wellbore fluid according to claim 1, wherein both of the at least two distinct cyclic monomers have at least two heteroatoms in the cyclic structure.

3. The wellbore fluid according to claim 1, wherein the at least two heteroatoms are nitrogen.

4. The wellbore fluid according to claim 1, wherein one of the at least two distinct cyclic monomers is a halogenated monomer selected from the group consisting of cyanuric chloride having a benzene-ring containing halogenation in 1,3,5 positions, cyanuric chloride having a benzene-ring containing halogenation in 1,4 positions, halogenated compounds having a benzene-ring containing halogenation in 1,3,5 positions, and halogenated compounds having a benzene-ring containing halogenation in 1,4 positions.

5. The wellbore fluid according to claim 4, wherein the halogenated monomer is selected from the group consisting of:

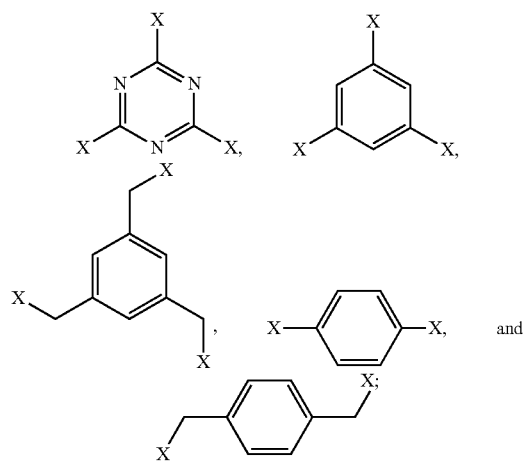

wherein each X is selected from Cl, Br, or I.

6. The wellbore fluid according to claim 1, wherein another of the at least two distinct cyclic monomers is a non-halogenated nitrogen-rich heterocycle.

7. The wellbore fluid according to claim 6, wherein the non-halogenated nitrogen-rich heterocycle is selected from the group consisting of 1,4-diazabicyclo[2.2.2]octane, hexamethylenetetramine, pyrazine and bipyridine, wherein a pyrazine or bipyridine is optionally substituted by hydroxyl or alkyl groups, or combinations thereof.

8. The wellbore fluid according to claim 1, wherein the two distinct cyclic monomers for CHPs have a molar ratio a halogenated monomer to a non-halogenated heterocycle ranging from 1:0.2 to 1:1.5.

9. The wellbore fluid according to claim 1, wherein the wellbore fluid has a plastic viscosity within a range from 10 to 120 cP at a temperature ranging from 72 F to 450 F, and a pressure ranging from 15 psi to 35000 psi.

10. The wellbore fluid according to claim 1, wherein the wellbore fluid has a yield point that is within a range from 2 to 50 lb/100 ft$^2$ at a temperature ranging from 72 F 450 F, and under a pressure ranging from 15 psi to 35000 psi.

11. The wellbore fluid of claim 1, wherein the CHP is present in an amount ranging from 0.2 to 3 g/mL of the base fluid.

12. The wellbore fluid of claim 1, wherein a backbone of the CHP extends in at least two dimensions.

\* \* \* \* \*